US00PP07866P

United States Patent [19]

de Jong

[11] Patent Number: Plant 7,866

[45] Date of Patent: May 12, 1992

[54] BOUVARDIA NAMED STEPHANIE

[76] Inventor: John M. F. de Jong, Floraweg 67, 2371 AM Roelofarendsveen, Netherlands

[21] Appl. No.: 619,022

[22] Filed: Nov. 28, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Harold L. Jackson

[57] ABSTRACT

A new Bourvardia variety characterized by the large, fragrant, single flowers. The blooms are unique in size with a stronger throat that has better lasting qualities.

1 Drawing Sheet

BACKGROUND OF THE NEW PLANT

This new Bouvardia originated as a mutation from the breeding stock plant Longiflora. The particular mutation was selected by me in 1989 for propagation and testing because of the distinctive flower form. Specifically, the flower is a four lobed tubular corolla. It is pure white in color. The selected plant was propagated by me in Roelofarendsveen, Holland through several generations of cutting propagation to establish that its distinctive characteristics hold true from generation to generation and appear to be firmly fixed.

Breeding efforts commenced 1984 in Roelofarendsveen, Holland where the breeding stock is maintained. My new variety, Stephanie, differs from other variations, in that it has a unique large white fragrant flower with a strong throat for better lasting quality.

DESCRIPTION OF THE DRAWING

This new variety of the Bouvardia plant is illustrated by the accompanying photograph which shows a blooming cyme of the plant with buds and flowers in various stages of opening.

DESCRIPTION OF THE NEW PLANT

The following is a detailed description of my new Bouvardia plant with color designations according to The National Bureau of Standards, Standard Reference Material, #2107, comprising the ISCC-NBS Centroid Color Charts and NBS Special Publication, #440.

THE PLANT

Origin: Mutation.
Parentage: Stock plant.
Classification: Rubiaceae family.
Form: A vigorously growing small shrub with leaves arranged opposite and flowers in terminal cymes.
Height: Up to 80.0 cm.
Growth: Vigorous.
Root stock: Rhizome.
Foliage:
- *Quantity.*—Many.
- *Number of leaves.*—10–15 per stem.
- *Size of leaf.*—About 6.0 cm.
- *Shape of leaf.*—Lanceolate.
- *Texture.*—Smooth.
- *Color.*—Upper side: Green. Under side: Green.

THE BUD

Form: Flask-shaped.
Size: Small.
- *Diameter.*—About 1.0 cm.
- *Length.*—About 7.0 cm.

Peduncle:
- *Length.*—About 8.0 cm.
- *Texture.*—Smooth.
- *Form.*—Erect.

THE FLOWER

Blooming habit: Continuously year-round.
Flower size:
- *Diameter.*—About 3.0 cm.
- *Depth.*—About 7.0 cm.

Borne: Terminal cymes.
Shape: Lobed tubular corolla.
Petalage:
- *Number of petals.*—Four.
- *Arrangement.*—Concentric circle.
- *Form.*—Elliptical.
- *Texture.*—Smooth.
- *Appearance.*—Satiny.

Color: White (No. 263).
Persistance: The flowers hang on and dry.
Main stem or stalk:
- *Length.*—Up to 80.0 cm.
- *Color.*—Green.
- *Character.*—Sturdy and erect.

Lasting quality of flower: About 25 days. As a cut flower 14 days.

REPRODUCTIVE ORGANS

Stamens:
- *Number.*—Four.
- *Arrangement.*—Alternate with corolla lobes.

Anthers:
- *Size.*—About 0.25 cm.
- *Color.*—White (No. 263).

Filaments:
- *Length.*—About 1.0 cm.
- *Color.*—White (No. 263).
- *Pollen.*—White (No. 263).

Pistils:
- *Number.*—One.
- *Styles.*—Length: About 1.0 cm. Color: White (No. 263).

Fruit:
- *Shape.*—Loculicidal capsule, seeds winged.

*Color.*—Brown.

This plant is particularly noted for the distinctive size and lasting quality of its flowers, which size and lasting quality does not clearly resemble that of any other Bouvardia plant previously known to me.

I claim:

1. A new and distinctive Bouvardia cultivar, substantially as herein shown and described, characterized by the distinctive coloration of its profusely blooming flowers.

* * * * *

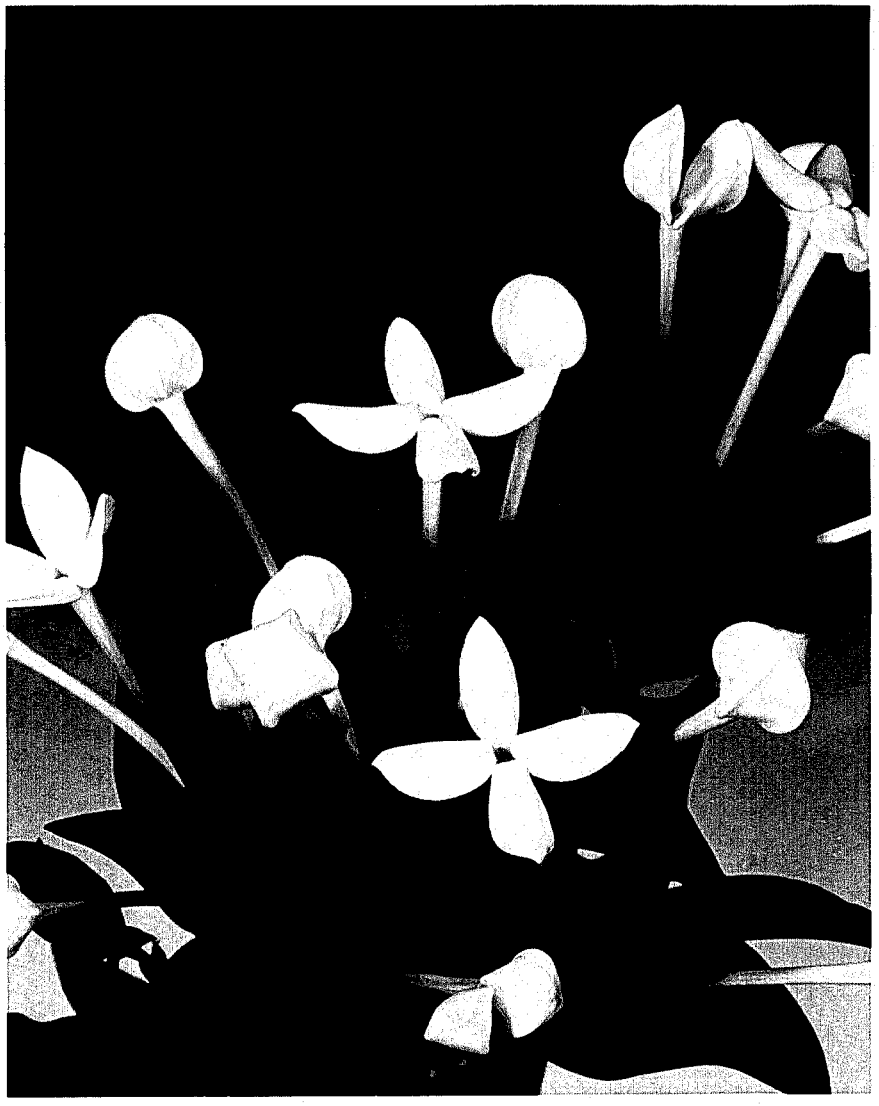

UNITED STATES PATENT AND TRADEMARK OFFICE

CERTIFICATE OF CORRECTION

PATENT NO. : Plant 7,866

DATED : May 12, 1992

INVENTOR(S) : John M. F. de Jong

It is certified that error appears in the above-identified patent and that said Letters Patent is hereby corrected as shown below:

Column 1, lines 16 and 17, "variations" should read --varieties--.

Column 2, line 26, "Persistance" should read --persistence--.

Signed and Sealed this

Twenty-ninth Day of June, 1993

Michael K. Kirk

*Attest:*

MICHAEL K. KIRK

*Attesting Officer*

*Acting Commissioner of Patents and Trademarks*